US011020181B2

(12) United States Patent
Kubota et al.

(10) Patent No.: US 11,020,181 B2
(45) Date of Patent: Jun. 1, 2021

(54) INFRARED DENATURING DEVICE

(71) Applicant: Educational Foundation Kyorin Gakuen, Tokyo (JP)

(72) Inventors: Hiroshi Kubota, Tokyo (JP); Masahiko Hoshino, Saitama (JP)

(73) Assignee: Educational Foundation Kyorin Gakuen, Tokyo (JP)

( * ) Notice: Subject to any disclaimer, the term of this patent is extended or adjusted under 35 U.S.C. 154(b) by 372 days.

(21) Appl. No.: 16/068,105

(22) PCT Filed: Jan. 6, 2017

(86) PCT No.: PCT/JP2017/000283
§ 371 (c)(1),
(2) Date: Jul. 3, 2018

(87) PCT Pub. No.: WO2017/119487
PCT Pub. Date: Jul. 13, 2017

(65) Prior Publication Data
US 2019/0029755 A1 Jan. 31, 2019

(30) Foreign Application Priority Data
Jan. 7, 2016 (JP) .............................. JP2016-001471

(51) Int. Cl.
*A61B 17/04* (2006.01)
*A61B 18/18* (2006.01)
(Continued)

(52) U.S. Cl.
CPC ............ *A61B 18/18* (2013.01); *A61B 18/201* (2013.01); *A61N 5/06* (2013.01); *A61N 5/0601* (2013.01);
(Continued)

(58) Field of Classification Search
CPC ................. A61B 18/18; A61B 18/201; A61B 2018/00875; A61B 2018/00708;
(Continued)

(56) References Cited

U.S. PATENT DOCUMENTS 4,233,493 A 11/1980 Nath
4,539,987 A 9/1985 Nath et al.
(Continued)

FOREIGN PATENT DOCUMENTS

JP H02-21856 A 1/1990
JP H06-261910 A 9/1994
(Continued)

OTHER PUBLICATIONS

International Search Report dated Feb. 21, 2017 during the prosecution of PCT/JP2017/000283.
(Continued)

*Primary Examiner* — Mallika D Fairchild
(74) *Attorney, Agent, or Firm* — Troutman Pepper Hamilton Sanders LLP

(57) ABSTRACT

The infrared denaturing device of the present invention is provided with: an infrared lamp which emits infrared light; a light guide which guides the infrared light; and a light projecting body which radiates the infrared light guided from the light guide onto an object to be denatured. The light projecting body is provided with: a reflecting surface which reflects the infrared light; and a radiating surface which radiates the infrared light reflected by the reflecting surface onto an object to be irradiated. Further, there is also provided a denaturing detection sensor which detects denaturing, by means of the infrared light, of a region being denatured.

23 Claims, 16 Drawing Sheets

(51) Int. Cl.
*A61B 18/20* (2006.01)
*A61N 5/06* (2006.01)
*A61B 18/00* (2006.01)
*A61B 17/00* (2006.01)

(52) U.S. Cl.
CPC .............. *A61B 2017/00022* (2013.01); *A61B 2017/00026* (2013.01); *A61B 2017/00128* (2013.01); *A61B 2017/00199* (2013.01); *A61B 2017/00973* (2013.01); *A61B 2018/00017* (2013.01); *A61B 2018/00351* (2013.01); *A61B 2018/00363* (2013.01); *A61B 2018/00589* (2013.01); *A61B 2018/00642* (2013.01); *A61B 2018/00648* (2013.01); *A61B 2018/00708* (2013.01); *A61B 2018/00738* (2013.01); *A61B 2018/00791* (2013.01); *A61B 2018/00821* (2013.01); *A61B 2018/00839* (2013.01); *A61B 2018/00875* (2013.01); *A61B 2018/1807* (2013.01); *A61B 2018/2005* (2013.01); *A61B 2018/20553* (2017.05); *A61N 2005/0654* (2013.01); *A61N 2005/0659* (2013.01); *A61N 2005/0666* (2013.01)

(58) Field of Classification Search
CPC ........... A61B 2018/20553; A61B 2018/00821; A61B 2018/00642; A61B 2018/00738; A61B 2018/2005; A61B 2018/00017; A61B 2018/00363; A61B 2018/00859; A61B 2018/00648; A61B 2018/00791; A61B 2018/00839; A61B 2018/1807; A61B 2017/00022; A61B 2017/00026; A61B 2017/00128; A61B 2017/00199; A61B 2017/00973; A61N 5/0601; A61N 5/06; A61N 2005/0654; A61N 2005/0659; A61N 2005/0666
See application file for complete search history.

(56) References Cited

U.S. PATENT DOCUMENTS

| | | | |
|---|---|---|---|
| 4,884,568 A | 12/1989 | Hahn | |
| 5,254,114 A | 10/1993 | Reed, Jr. et al. | |
| 7,977,658 B2 | 7/2011 | Stuba et al. | |
| 2002/0143326 A1* | 10/2002 | Foley | A61B 18/1492 606/41 |
| 2003/0220639 A1 | 11/2003 | Chapelon et al. | |
| 2007/0156209 A1 | 7/2007 | Laufer et al. | |
| 2008/0308753 A1* | 12/2008 | Stuba | A61B 18/18 250/504 R |
| 2009/0240242 A1 | 9/2009 | Neuberger | |
| 2010/0298826 A1 | 11/2010 | Leo et al. | |
| 2012/0022510 A1* | 1/2012 | Welches | A61B 18/22 606/3 |
| 2012/0029504 A1 | 2/2012 | Afonso et al. | |
| 2012/0071870 A1 | 3/2012 | Salahieh et al. | |
| 2014/0025066 A1* | 1/2014 | Kerr | G01D 5/35316 606/34 |
| 2014/0243808 A1* | 8/2014 | Molnar-Hammond | A61B 18/1477 606/23 |
| 2014/0243821 A1 | 8/2014 | Salahieh et al. | |
| 2014/0026623 A1 | 9/2014 | Kim et al. | |
| 2014/0266235 A1 | 9/2014 | Mathur | |

FOREIGN PATENT DOCUMENTS

| | | |
|---|---|---|
| JP | 2010-509022 A | 3/2010 |
| JP | 2010-529885 A | 9/2010 |
| JP | 2010-259810 A | 11/2010 |
| JP | 2011-512965 A | 4/2011 |
| JP | 2013-529109 A | 7/2013 |
| JP | 2014-504896 A | 2/2014 |
| JP | 2014-531935 A | 12/2014 |
| WO | 2008/156623 A1 | 12/2008 |
| WO | 2014149690 A2 | 9/2014 |

OTHER PUBLICATIONS

Kubota, et al., Ann Thorac Sueg.(The Society of Thoracic Surgeons) pp. 95-100 (1998).
Kubota, et al., The Journal of Cardiovascular Surgerypp. 835-847 (2000).
Kubota, et al., Ann Thorac Sueg.(The Society of Thoracic Surgeons) pp. 1081-1086 (2004).
Kubota, et al., Atrial Fibrillation ,INTECH, pp. 267-290 (2011).
Kubota, et al., Ann Thorac Sueg.(The Society of Thoracic Surgeons) pp. 1592-1595 (2009).
Kubota, H., et al. "Epicardial Maze Procedure on the Beating Heart With an Infrared Coagulator" Ann Thorac Surg 80:1081-1086 (2005) cited in EESR issued in Appln. No. 17736024.5 dated Jul. 23, 2019.
Extended European Search Report issued in corresponding European Patent Application No. 17736024.5 dated Jul. 23, 2019.

* cited by examiner

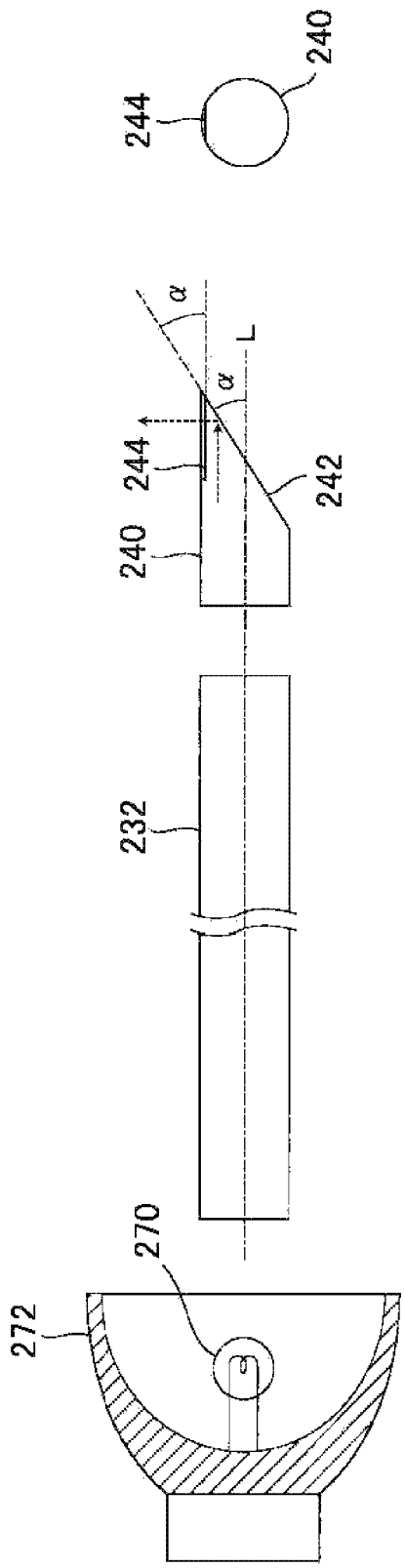

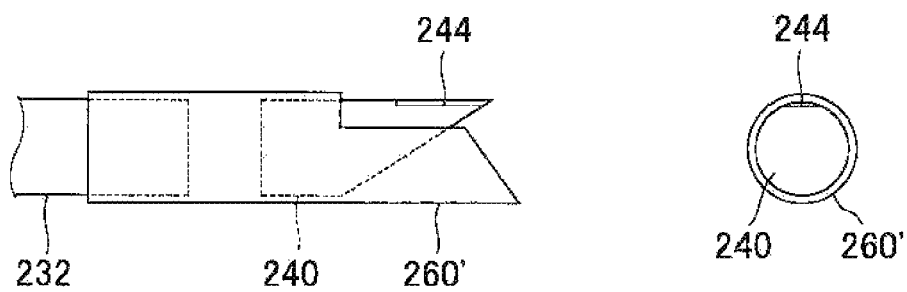
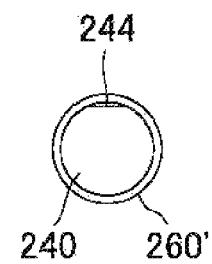
Fig. 5A
Fig. 5B

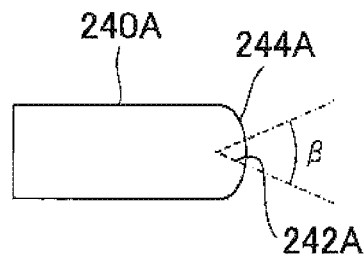
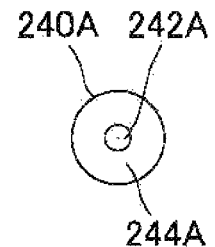
Fig. 6A        Fig. 6B
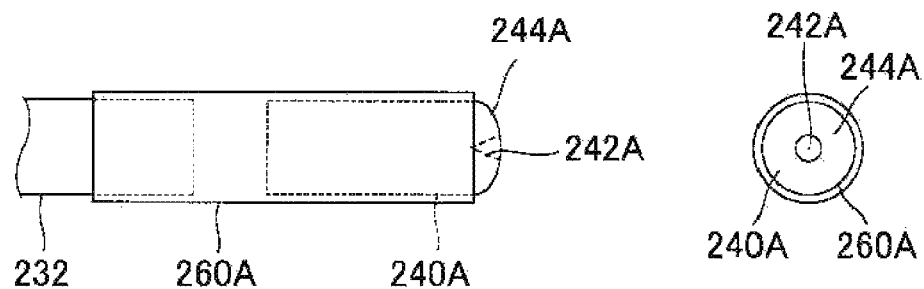
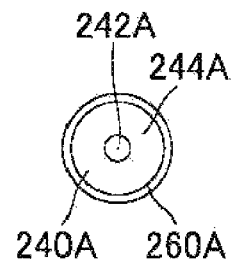
Fig. 6C        Fig. 6D

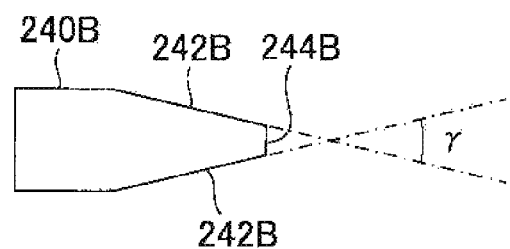
*Fig. 7A*
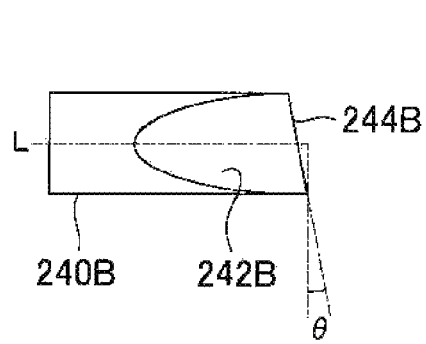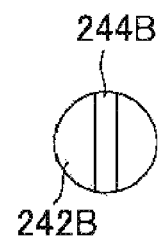
*Fig. 7B*  *Fig. 7C*
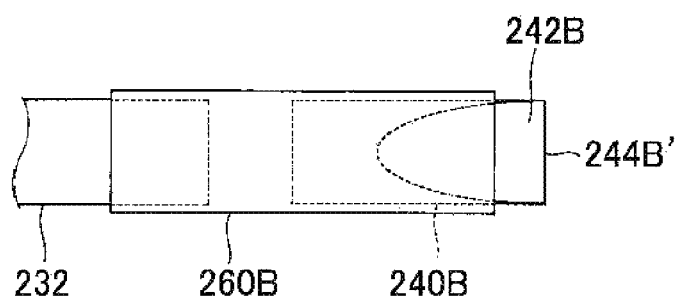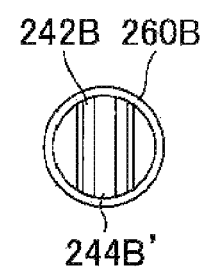
*Fig. 7D*  *Fig. 7E*

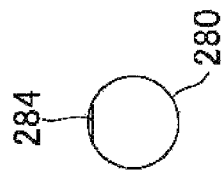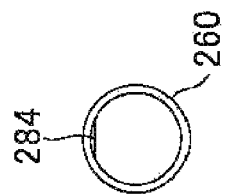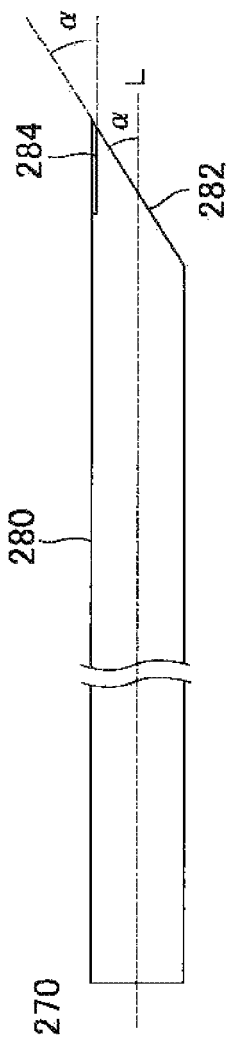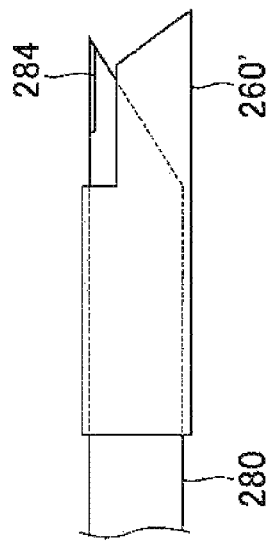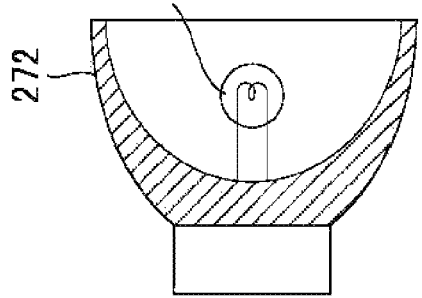

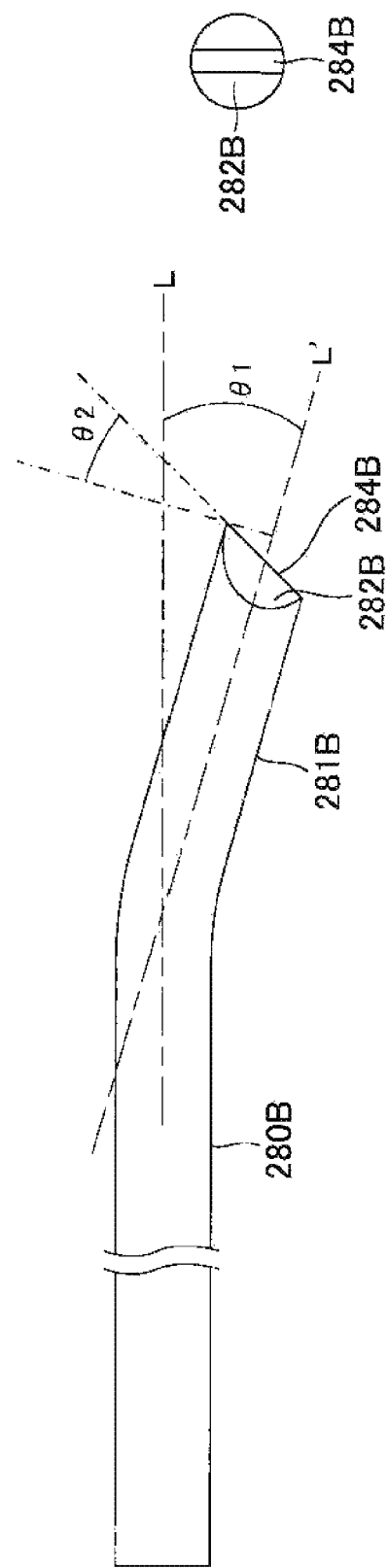

INFRARED DENATURING DEVICE

CROSS-REFERENCE TO RELATED APPLICATIONS

This is a U.S. national phase application under 35 U.S.C. § 371 of International Patent Application No. PCT/JP2017/000283, filed Jan. 6, 2017, and claims benefit of priority to Japanese Patent Application No. 2016-001471, filed Jan. 7, 2016. The entire contents of these applications are hereby incorporated by reference.

FIELD OF TECHNOLOGY

The present invention relates to an infrared denaturing device used for surgical operations, and more particularly, to an infrared denaturing device (infrared coagulator) for carrying out atrial coagulation upon a surgical treatment for atrial fibrillation.

BACKGROUND

Surgical treatments for atrial fibrillation (MAZE surgery) are widely carried out in general, where various atrium coagulators have been developed for shortening the operation time to replace the operation of cutting and suturing the atrium by the so-called original cut-and-sew method. Radiofrequency (RF), cryothermy, microwave, ultrasound and laser are known as the energy sources used for atrial ablation upon MAZE surgery, which are each undergoing development for clinical application. However, transmural coagulation has not yet been achieved by radiation with these energy sources onto the beating heart solely via an epicardial approach.

While current mainstream coagulators use RF, they require a manipulation of "sandwiching" the atrium upon coagulation. Furthermore, RF may cause damage of the epicardium or transpiration of the tissue, which may result in perforation. Although cryothermy is very useful while the heart is stopped, a so-called radiator effect (heat sink) is caused in a normothermic beating heart where the blood flow at normal temperature deprives the cooling heat and thus coagulation cannot be achieved on the endocardium side.

Meanwhile, as will be described below, since an infrared atrium coagulator developed by the present inventors, unlike other energy sources, is characterized by being capable of achieving transmural atrial coagulation in a short time by radiation onto the beating heart solely via an epicardial approach, it can also be applied to less invasive atrial fibrillation surgery and ventricular tachycardia (VT) ablation using a thoracoscope.

As a prototype of the infrared coagulator, IRK-151 (In-frarot-Kontaktkoagulator; Messerschmidt-Bolkow-Blown, Frankfurt, Germany) was used. IRK151 was originally developed and clinically applied in place of electrosurgical scalpels and laser to stop bleeding from the mucosal surface. IRK151 is provided with a 3-second radiation timer, where infrared energy from a tungsten halogen lamp is converged with a reflector and emerges via a quartz rod as infrared light having a 10-mm circular cross-section. The wavelength of the electromagnetic wave emitted from the tungsten halogen lamp is 400-1600 nm while the peak wavelength is 850 nm though the infrared light partially contains visible light. Coagulation/denaturation is histologically caused at an infrared wavelength.

As reported in Kubota et al., Atrial Ablation With an IRK-151 Infrared Coagulator, Ann Thorac Sueg., 1998 95-100 by the present inventors, IRK-151 was used as a coagulator in an animal experiment to see whether this coagulator can create a conduction block in the atrium. Mongrel dogs were used to irradiate the right atrium from both the endocardial and epicardial sides and electrophysiological mapping was conducted before and after the radiation, by which creation of a bidirectional conduction block was confirmed. Moreover, an irradiation experiment on the ventricular wall confirmed that a maximum of 12 mm transmural coagulation can be achieved with 21 seconds of irradiation.

As the next step, as reported by the present inventors in Kubota et al., Atrial Ablation Using an IRK-151 Infrared Coagulator in Canine Model, J Cardiovasc Surg., 2000 835-847, dogs were subjected to an atrial fibrillation surgery experiment using a heart-lung machine while the heart was stopped to prove that MAZE surgery can be realized with infrared coagulation.

Although the experiments so far were conducted using a coagulator prototype based on IRK-151, the prototype seemed to need improvements with respect to the following points for clinical applications: (1) the timer is only 3 seconds at most; (2) the handheld equipment body of the coagulator is made from plastic which may be thermally deformed over long time use; and (3) radiation energy cannot be controlled.

Accordingly, as reported by the present inventors in Kubota et al., Epicardial Maze Procedure on the Beating Heart With an Infrared Coagulator, Ann Thorac Surg., 2004 1081-1086, a second-generation coagulator was developed as follows: (1) the radiation timer was extended to 40 seconds; (2) the handheld equipment body was made with a heat resistant metal; and (3) a variable capacitor was incorporated to allow variation of outputs. Five mongrel dogs were used to confirm the effect of this coagulator. As a result, a stimulation conduction block similar to the cutting and suturing line in the MAZE surgery was created in the atrial free wall (except the atrial septum) of the beating heart from the epicardium side, where the atrial fibrillation that was induced before the surgery was no longer induced after the surgery.

SUMMARY OF INVENTION

An improvement required for the second-generation coagulator is that since the shape of the light emitting end surface of the tip probe is a 10-mm circle, and the light emitting surface is small for use in a human, requiring multiple times of radiation for linear or belt-like irradiation and thus taking a long time for the surgery. Therefore, in order to realize efficient coagulation of the biological tissue such as the myocardium, the present invention has an objective of providing an infrared denaturing device having a light emitting surface with a more optimal shape.

In order to perform interruptive blocking of the abnormal conductive pathway by tissue coagulation of the myocardial tissue from the epicardium side, a device that can control the size and the depth of the coagulation is required. However, a device that is capable of forming a transmural coagulation in a length generally extending 30 millimeters or deep in the depth direction of the atrial wall has a problem of carbonization (blackening) denaturation resulting from a histological reaction of the surface layer, and thus is unavailable under the present circumstances. In addition, since coagulation may be performed on the beating heart using a myocardial thoracoscope or the like, stable handling of the light emitting end surface in a narrow operational field and a function of ensuring blocking of the supposed area with one shot are also required.

Coagulation of the myocardial tissue not only requires histological denaturation that can be confirmed by direct observation but also importantly requires management of the spread and depth of the denaturation underneath, and management of the boundary with the normal area. Even if coagulation is repeatedly performed on the surface layer of the myocardial tissue with a coagulator so as to visually cover the entire targeted area, interruptive blocking of the abnormal conductive pathway, a sterilization treatment against the bacterial layer and coagulation procedure for malignant cells intended would be incomplete if continuity of the coagulation is disturbed underneath the surface layer of the myocardial tissue. The present invention has an objective of providing an infrared denaturing device that allows an operator to perform denaturation while recognizing the denaturing state such as the coagulation depth.

Each aspect of the present invention is composed as follows.

(Aspect 1) An infrared denaturing device for denaturing an object to be denatured with infrared light, the infrared denaturing device comprising an infrared light source for emitting non-directional infrared light, a light projecting body for irradiating a region being denatured of the object to be denatured with infrared light, and a controller for controlling the operation of the infrared light source, wherein the light projecting body is provided, at its tip on the light emitting side, with at least one pair of a reflecting surface for reflecting and guiding infrared light from the infrared light source to the region being denatured and a light emitting surface for emitting the infrared light reflected by the reflecting surface onto the region being denatured; and wherein the infrared denaturing device is provided with a denaturation detecting sensor for detecting infrared denaturation of the region being denatured.

(Aspect 2) The infrared denaturing device according to Aspect 1, wherein the denaturation detecting sensor is an electrical stimulation interruption confirming sensor for confirming interruption of electrical stimulation in the region being denatured. (Aspect 3) The infrared denaturing device according to Aspect 2, wherein the interruption confirming sensor comprises, in the vicinity of the region being denatured, a pair of contact terminals that make contact with the object to be denatured. (Aspect 4) The infrared denaturing device according to Aspect 3, wherein the pair of contact terminals are disposed to sandwich the light emitting surface at the long sides of the light emitting surface. (Aspect 5) The infrared denaturing device according to either one of Aspects 3 and 4, wherein the interruption confirming sensor measures conduction time of electrical stimulation between the pair of contact terminals. (Aspect 6) The infrared denaturing device according to Aspect 5, wherein the controller judges completion of denaturation of the region being denatured based on the conduction time. (Aspect 7) The infrared denaturing device according to any one of Aspects 3-6, wherein the pair of contact terminals are disposed distant from the light emitting surface so as to avoid influence of the infrared light from the light emitting surface.

(Aspect 8) The infrared denaturing device according to any one of Aspects 1 to 7, further comprising a temperature sensor for measuring the temperature of the region being denatured or the light emitting surface. (Aspect 9) The infrared denaturing device according to Aspect 8, wherein the controller calculates the coagulation depth of the region being denatured by using the temperature information acquired with the temperature sensor and an output density and radiation time of the infrared light. (Aspect 10) The infrared denaturing device according to Aspect 9, comprising a display device for displaying the calculated coagulation depth.

(Aspect 11) An infrared denaturing device for denaturing an object to be denatured with infrared light, the infrared denaturing device comprising an infrared light source for generating non-directional infrared light, a light projecting body for irradiating a region being denatured of the object to be denatured with infrared light, and a controller for controlling the operation of the infrared light source, wherein the light projecting body is provided, at its tip on the light emitting side, with at least one pair of a reflecting surface for reflecting and guiding infrared light from the infrared light source to the region being denatured and an elongated light emitting surface for emitting the infrared light reflected by the reflecting surface onto the region being denatured.

(Aspect 12) The infrared denaturing device according to any one of Aspects 1 to 11, wherein the light emitting surface has long sides of about 8-40 mm. (Aspect 13) The infrared denaturing device according to any one of Aspects 1 to 12, wherein the reflecting surface diffuses, disperses or totally reflects the infrared light from the infrared light source. (Aspect 14) The infrared denaturing device according to any one of Aspects 1 to 13, wherein the reflecting surface is inclined to the light guide axis of the infrared light from the infrared light source to the light projecting body, and the light emitting surface is disposed generally in parallel to the light guide axis. (Aspect 15) The infrared denaturing device according to any one of Aspects 1 to 14, wherein the tip of the light projecting body on the light emitting side is formed to have a dome shape or a semi-circular shape, the reflecting surface is formed to have a conical shape in a recess provided at the center of the tip of the light projecting body on the light emitting side, and the light emitting surface is formed along the dome shape or the semi-circular shape.

(Aspect 16) The infrared denaturing device according to any one of Aspects 1 to 15, wherein the reflecting surface is a pair of reflecting surfaces formed at the tip of the light projecting body, and the light emitting surface is disposed between the pair of reflecting surfaces and formed generally at a right angle or inclined to the light guide axis. (Aspect 17) The infrared denaturing device according to any one of Aspects 1 to 16, wherein a light guide for guiding infrared light emitted from the infrared light source to the light projecting body is integrally formed with the light projecting body. (Aspect 18) The infrared denaturing device according to Aspect 17, wherein the light guide is a rectangular prism with a rectangular cross section, the reflecting surface is a pair of reflecting surfaces provided at the long sides of the tip on the light emitting side, and the light emitting surface is a rectangular light emitting surface formed between the pair of reflecting surfaces.

(Aspect 19) The infrared denaturing device according to any one of Aspects 1 to 18, comprising a heat-proof guard guide provided at the tip of the light projecting body on the light emitting side in order to prevent infrared irradiation of the region not being denatured of the object to be denatured. (Aspect 20) The infrared denaturing device according to Aspect 19, wherein the guard guide is provided with a notch for irradiating the region being denatured with infrared light.

(Aspect 21) An infrared denaturing method for denaturing an object to be denatured with infrared light by using the infrared denaturing device according to any one of Aspects 1 to 20, the method comprising an irradiation step of irradiating the region being denatured with infrared light while pressing the light emitting surface onto the surface of the region being denatured of the object to be denatured. (Aspect 22) The infrared denaturing method according to Aspect 21, wherein the irradiation step is repeated for multiple times to form an elongated denatured region. (Aspect 23) The infrared denaturing method according to either one of Aspects 21 and 22, wherein the object to be denatured is a heart, and the irradiation step comprises irradiating the region being denatured of the object to be denatured with infrared light while pressing the light emitting surface onto the heart from the epicardium side. (Aspect 24) The infrared denaturing method according to Aspect 23, wherein the irradiation step is carried out under a beating heart condition. (Aspect 25) An infrared denaturing device for denaturing an object to be denatured with infrared light, the device comprising: a light projecting body for emitting the infrared light while making contact, in a substantially rectangular shape, with a region being denatured of the object to be denatured; an interruption confirming sensor having a pair of contact terminals that are distantly disposed outside the region being denatured along a line crossing the longitudinal direction of the contact part of the light projecting body; and a controller provided with a stimulation conduction time measuring section for carrying out measurement based on conduction time of an electrical stimulation signal that is sent from outside the region being denatured via the first contact terminal of the interruption confirming sensor and that is received with the second contact terminal, and a radiation controller for emitting infrared light to the light projecting body at predetermined intervals or duty cycle. (Aspect 26) A method for controlling irradiation by an infrared denaturing device for denaturing an object to be denatured with infrared light, the method comprising the steps of: irradiating a region being denatured of the object to be denatured with infrared light at predetermined intervals or duty cycle while allowing the light projecting body to make contact therewith in a generally rectangular shape; sending an electrical stimulation signal to a first contact terminal of a pair of contact terminals that are distantly disposed outside the region being denatured along a line crossing a longitudinal direction of a contact part of the light projecting body; receiving the conduction signal of the electrical stimulation signal sent to the object to be denatured on the opposite side relative to the longitudinal direction of the rectangular light projecting body; and judging completion of coagulation by infrared denaturation after detecting stability of the conduction time during and after the operation with respect to the conduction time of the electrical stimulation signal before the operation.

BRIEF DESCRIPTION OF DRAWINGS

FIG. 3A A schematic view showing an infrared light generating and transmitting structure according to the first embodiment.

FIG. 3B A schematic view showing an infrared light generating and transmitting structure in the axial view according to the first embodiment.

FIGS. 5A-5B A view showing a variation of the guard guide according to the first embodiment.

FIGS. 6A-6D A view showing a light projecting body according to a second embodiment.

FIGS. 7A-7E A view showing a light projecting body according to a third embodiment.

FIGS. 8A-8D A schematic view showing a light guide which is integrated with a light projecting body according to a fourth embodiment.

FIGS. 9A-9B A schematic view showing a light guide which is integrated with a light projecting body according to a fifth embodiment.

DETAILED DESCRIPTION

An infrared denaturing device (infrared coagulator) of the present invention is used for performing a treatment and the like by generating partial denaturation (coagulation) onto a part of a biological tissue during a surgery or a therapeutic treatment. In each of the embodiments of the present invention, a case where the infrared denaturing device of the present invention is applied to a surgical treatment of atrial fibrillation will be illustrated. The infrared denaturing device of the present invention, however, is not limited to a surgical treatment of atrial fibrillation, and can also be employed, for example, as a coagulation cautery for a relatively minor mucous membrane like a rectal mucous membrane such as a hemorrhoid, a uterine cervical mucous membrane in the fields of obstetrics and gynecology, and oral and nasal cavity mucous membranes in the fields of stomatology and otorhinolaryngology. Herein, in each embodiment, description of the same components as the first embodiment will suitably be omitted and components different from the first embodiment will be described.

First Embodiment

Figure 1:
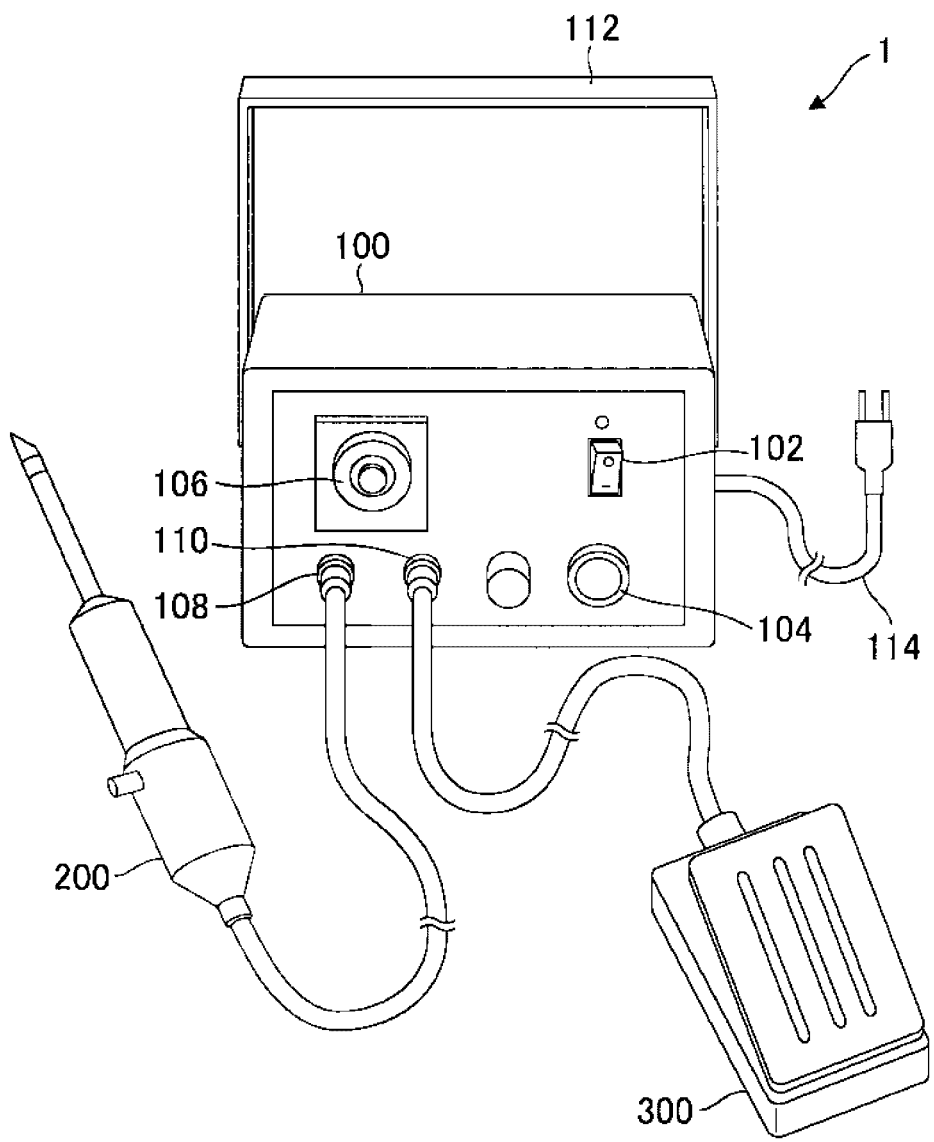
FIG. 1 A perspective view of an infrared denaturing device according to a first embodiment of the present invention.

An infrared denaturing device according to a first embodiment of the present invention will be described with reference to FIGS. 1-5. An infrared denaturing device 1 shown in FIG. 1 is provided with a device body 100 equipped with various switches, a handheld equipment 200 for emitting infrared light, and a foot switch 300 for controlling infrared radiation. The device body 100 is provided with a power switch 102 for turning the power source on and off, an infrared radiation switch 104 for controlling infrared radiation, a timer 106 for setting infrared radiation time, a handheld equipment connector 108 connected to a cable of the handheld equipment 200, a foot switch connector 110 connected to a cable of the foot switch 300, a handle 112 rotatably attached to the device body 100, and a power cord 114 connected to an external power supply.

Figure 2:
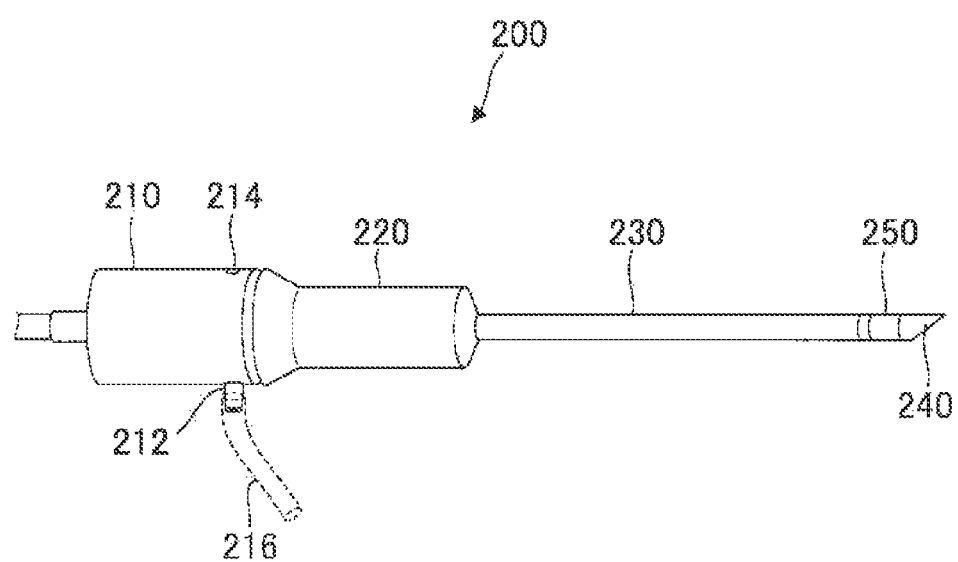
FIG. 2 A side view showing a handheld equipment of the infrared denaturing device shown in FIG. 1.

The handheld equipment 200 shown in FIG. 2 is provided with a hollow body part (lamp house) 210 for accommodating an infrared lamp, a grip member 220 connected to the right end (infrared outputting end) of the body part 210, a light guide accommodating member 230 connected to the right end (infrared outputting end) of the grip member 220, a light projecting body 240 disposed at the right end (infrared outputting end) of the light guide accommodating member 230, and a connection cylinder 250 for connecting the light guide accommodating member 230 with the light projecting body 240. Preferably, one end of the connection cylinder 250 is fixedly attached to the tip of the light guide accommodating member 230 while the other end of the connection cylinder 250 detachably holds the light projecting body 240.

Preferably, the body part 210 can be formed of a heat-resistant member such as a metal and further be equipped with a cooling mechanism to withstand the heat generated by the infrared lamp. This cooling mechanism may, for example, be an air-cooled cooling mechanism, which includes a suction pipe 212 for sucking the air inside the body part 210, an outside air intake 214 for allowing the outside air to enter the body part 210, a flexible suction tube 216 connected to the suction pipe 212, and a suction pump (not shown) connected to the suction tube 216. The body part 210 generates heat upon operating the infrared lamp, but as the air inside is suctioned via the suction pipe 212, outside air (air at room temperature) flows into the body part 210 via the outside air intake 214 to cool the entire handheld equipment, in particular, the infrared lamp and the body part.

The grip member 220 and the light guide accommodating member 230 are preferably cylindrical, inside which they accommodate a columnar light guide 232 which will be described later. The grip member 220 and the light guide accommodating member 230 are made from a metal or a resin to have a pipe shape so as to rigidly hold the light guide while preventing infrared light from leaking therefrom. Preferably, the surface of the grip member 220 is provided with an anti-slipping member such as a rubber, or the surface of the grip member 220 may be applied with an embossed anti-slipping work. Furthermore, the grip member 220 and/or the light guide accommodating member may be provided with a heat insulating layer such as glass wool.

Figure 11:
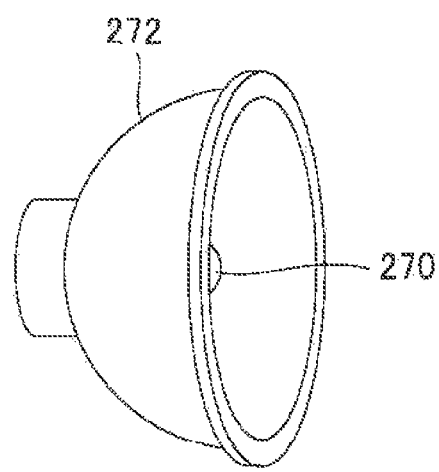
FIG. 11 A perspective view of a reflector attached to an infrared lamp used in each embodiment.

FIG. 3A shows an infrared light generating and guiding structure accommodated in the handheld equipment 200. In FIG. 3A, the body part 210, the grip member 220, the light guide accommodating member 230 and the connection cylinder 250 are not shown. FIG. 3B is a view of the light projecting body 240 seen in the axial direction L (longitudinal direction or incident direction). The back of the infrared lamp 270 is provided with a reflector 272. The reflector 272 has a curved reflecting surface as shown in the perspective view of FIG. 11. The infrared lamp 270 and the reflector 272 are accommodated in the body part 220. The light guide 232 is made from a material that allows transmission of infrared light, for example, a colorless and transparent material made from $SiO_2$ or $Al_2O_3$. The dimensions of the light guide 232 are, for example, a diameter of about 3.0-15 mm and a length of about 100-400 mm with a columnar shape. The both end surfaces of the light guide 232 are formed vertical to the axial direction L and optically polished.

The light projecting body 240 is made from a material that allows transmission of infrared light, for example, a colorless and transparent material made from $SiO_2$ or $Al_2O_3$. The dimensions of the light projecting body 240 may be such that it has a diameter identical to and/or larger than the diameter of the light guide 232, with an axial direction length of about 10-50 mm. The left end surface (light incoming end surface) of the light projecting body 240 is formed vertical to the axial direction L and optically mirror-polished. A tilted right end surface (reflecting surface) 242 of the light projecting body 240 makes an angle α to the axial direction L, and reflects, preferably totally reflects, infrared light in a lateral direction (direction generally vertical to the longitudinal direction). Preferably, this reflecting surface 242 is optically mirror-polished so as to have a flat surface and/or a slightly concaved surface suitable to the size of the contact surface.

A light emitting surface 244 is formed on the side of the light projecting body 240 for emitting infrared light onto a tissue targeted for irradiation (hereinafter, a tissue) such as a myocardium. Preferably, the light emitting surface 244 is optically polished to have a mirror surface, a rough surface or the like suitable for the purpose, and disposed to make an angle α to the reflecting surface 242. This angle α may preferably be about 20° to 60°, and more preferably about 45°. Infrared light emitted from the infrared lamp 270 passes through the light guide 232, enters and passes through the light projecting body 240, is reflected and/or dispersed on the reflecting surface 242, and dispersedly guided to the light emitting surface 244 which is relatively large with the long sides being preferably about 10 millimeters or longer, whereby the entire area of the light emitting surface 244 radiates the infrared light onto the tissue. The purpose of this dispersion upon guiding is to generally average the output distribution without causing a partially high, biased output distribution on the light emitting surface which is relatively large with the long sides being preferably about 10 millimeters or longer. Thus, an irradiation environment that hardly causes carbonization denaturation of the tissue can be provided. A tissue can be irradiated with infrared light in a state where this light emitting surface 244 is facing or making contact with the tissue. The light projecting body of the first embodiment is a laterally-directed radiation type that emits infrared light from the side of the light projecting body.

Figure 4A:
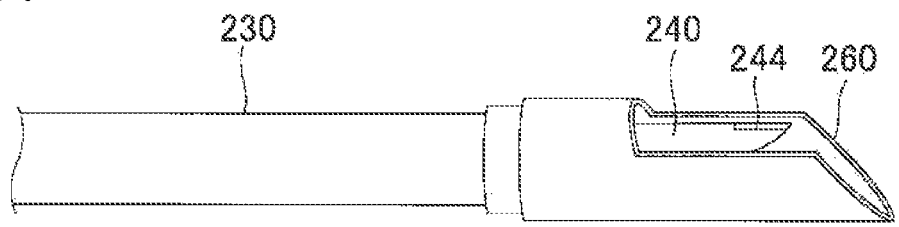
FIGS. 4A-4C A view showing a guard guide according to the first embodiment.
Figure 4B:
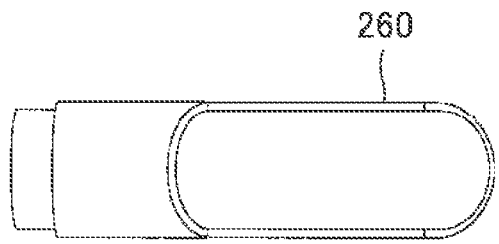
Figure 4C:
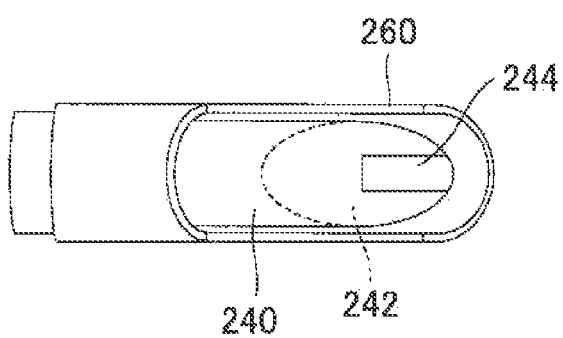

As shown in FIG. 4, the end of the light guide accommodating member 230 and the light projecting body 240 may be attached with a roughly cylindrical guard guide 260 having a notch on its side surface. With this notch on the light emitting surface side of the light projecting body, the guard guide 260 can expose the light emitting surface 244. In addition, the tip of the guard guide 260 is obliquely cut so as to facilitate insertion into a narrow site. The guard guide 260 is preferably made of a non-translucent member. The guard guide 260 is preferably made from a heat-resistant material and/or a heat-insulting material. Thus, light leakage and radiation heat to the outer periphery of the light emitting surface of the translucent chip can be interrupted or reduced.

Functions of the guard guide are as follows. First, it serves as a guard for interrupting the infrared light for the periphery of the tissue (tissue not targeted for coagulation) during irradiation of the tissue with infrared light emitted from the light emitting surface 244 of the light projecting body 240. Secondly, the guard guide is pressed onto the tissue to restrain the motion of the tissue (beating of the myocardium) so as to prevent dislocation between the light emitting surface and the tissue during infrared irradiation. Thirdly, it serves as a cover for safely inserting the light projecting body into the tissue targeted for irradiation. Here, the translucent chip and the guard guide may either be integrated or separately provided.

Next, a variation of the guard guide will be described. FIG. 5 shows the light projecting body 240 covered with a guard guide 260'. In FIG. 5(a), the light guide accommodating member 230 and the connection cylinder 250 are not shown. Since the guard guide 260' does not cover the tip of the light projecting body 240, the light emitting surface 244 of the light projecting body 240 can easily be pressed onto the tissue upon infrared irradiation.

Coagulation of a tissue with the infrared denaturing device 1 of the first embodiment will be described. The light emitting surface 244 of the light projecting body 240 is pressed onto a tissue targeted for coagulation such as a myocardium. The foot switch 300 or the infrared radiation switch 104 is manipulated while pressing the light emitting surface 244 so that infrared and visible light generated by the infrared lamp 270 is guided to the light projecting body 240 via the light guide 232. The infrared and visible light entering the light projecting body 240 is reflected by the reflecting surface 242 and radiates from the light emitting surface 244 to irradiate the tissue targeted for coagulation. The tissue targeted for coagulation is denatured and coagulated by the infrared energy. An example of a continuous radiation period may be 30 seconds. Preferably, a predetermined radiation time and a predetermined suspension time may be repeated within the continuous radiation period. For example, a duty cycle including 8 seconds of radiation and 2 seconds of suspension may be repeated for three times. Thus, a tissue having a large area can efficiently be coagulated in a linear or a belt-like manner by moving the light emitting surface during infrared irradiation of the tissue targeted for coagulation. Moreover, the handheld equipment 200 can efficiently be cooled with the cooling mechanism, which is preferably operated continuously during the continuous radiation period as well as after the irradiation for a predetermined time.

Second Embodiment

An infrared denaturing device according to a second embodiment of the present invention will be described with reference to FIG. 6. The infrared denaturing device according to the second embodiment differs from the infrared denaturing device of the first embodiment in the shapes of the light projecting body and the guard guide. In FIG. 6A is a side view of a light projecting body 240A, 6B is a front view of the light projecting body 240A seen from its tip, 6C is a side view of the light projecting body 240A attached with a guard guide 260A, and 6D is a front view of the light projecting body 240A in the state of 6C seen from its tip.

As shown in FIG. 6A, the light projecting body 240A is generally columnar with a round light emitting end, which is preferably shaped into a hemisphere or a dome. Furthermore, as shown in FIGS. 6A and 6B, a recess cut into a conical shape is formed in the center of the round light emitting end of the light projecting body 240, where this recessed surface (conical surface) serves as a reflecting surface 242A and the annular curved surface surrounding the recess serves as a light emitting surface 244A. When the movement of this light is studied in comparison to laser light, infrared light that spreads entirely within the light guide accommodating member 230 and the light guide at the incident end of the light projecting body 240 is totally reflected on the conical reflecting surface 242A so as to be dispersed and guided to the light emitting surface 244A. Since the light emitting surface 244A has an annular curved surface, it can radiate infrared light in the whole circumference direction. If this should be realized with laser light, even though total reflection that is high directive to a single direction can be realized, dispersion toward the whole circumference and/or uniform dispersion toward a wide area would be almost impossible considering operational accuracy in a narrow area. In FIG. 6C, the light guide accommodating member 230 and the connection cylinder 250 are not shown. As shown in FIG. 6C, the guard guide 260A is substantially cylindrical and is attached to the light projecting body 240A so as to expose the light emitting surface 244A of the light projecting body 240A. The recess configuring the reflecting surface 242A has a conical cut angle β at the cross section including the central axis line of the cone. This angle β can be set, for example, in a range of about 30°-90°.

Third Embodiment

An infrared denaturing device according to a third embodiment of the present invention will be described with reference to FIG. 7. The infrared denaturing device according to the third embodiment differs from the infrared denaturing device according to the first embodiment in the shapes of the light projecting body and the guard guide. In FIG. 7A is a top view of a light projecting body 240B, 7B is a side view of the light projecting body 240B, 7C is a front view of the light projecting body 240B in the state of 7B seen from its tip, 7D is a side view of the light projecting body 240B attached with a protection guard 260B, and 7E is a front view of the light projecting body 240B in the state of 7D seen from its tip.

As shown in FIGS. 7A-7C, the light projecting body 240B is a substantially columnar rod where the sides of the tip are cut off to form a pair of reflecting surfaces 242B. A tapered cut angle γ is formed between the reflecting surfaces 242B. This angle γ may be set, for example, in a range of about 30°-90°. The outer periphery of each of the reflecting surfaces 242B on the side surface forms a parabola as shown in FIG. 7B, the light emitting surface 244B has an angle θ that defines the light emitting surface with respect to a plane vertical to the axial direction L. This angle θ may be set, for example, in a range of about 0°-45°. The angle θ can be made larger to make the area of the light emitting surface larger. As shown FIG. 7C, the tip (right end) of the light projecting body 240B is formed to have a narrow substantially rectangular linear or belt-like light emitting surface 244B. The light emitting surface 244B is sandwiched between the pair of reflecting surfaces 242B. In addition, as can be appreciated from FIGS. 7A and 7B(b), the tip of the light projecting body 240B has an ax shape.

FIGS. 7D and 7E show the light projecting body 240B covered with the guard guide 260B. In FIG. 7D, the light guide accommodating member 230 and the connection cylinder 250 are not shown. The guard guide 260B is substantially cylindrical and covers the light projecting body 240B so as to expose the light emitting surface 244B' of the light projecting body 240B. In the shown case, the light emitting surface 244B' has an angle θ of 0.

Fourth Embodiment

An infrared denaturing device according to a fourth embodiment of the present invention will be described with reference to FIG. 8. The infrared denaturing device according to the fourth embodiment uses a light guide that is integrated with a light projecting body instead of the light guide and the light projecting body of the first embodiment. In FIG. 8A is a side view showing an infrared light generating and guiding structure, 8A is a front view of a light guide 280 in the state of 8A seen from its tip, 8C is a side view showing the light guide 280 having a guard guide 260' attached at its tip, and 8D is a front view of the light guide 280 in the state of 8C seen from its tip.

The light guide 280 shown in FIG. 8 is formed of a colorless transparent material which can transmit infrared light, for example, $SiO_2$ or $Al_2O_3$. The dimensions of the light guide 280 are, for example, a diameter of about 3.0-15 mm and a length of about 100-300 mm with a columnar shape. The incident end surface of the light guide 280 is formed vertical to the axial direction L and optically polished to have a mirror surface. As shown in FIG. 8A, a reflecting surface 282 is formed at the tip of the light guide 280. The reflecting surface 282 is formed to make an angle α to the axial direction L of the light guide 280 and optically polished. As shown in FIGS. 8A and 8B, a light emitting surface 284 for emitting infrared light to a tissue is formed on the side surface of the light guide 280 in the vicinity of the reflecting surface 282. The surface of the light emitting surface 284 is configured as an optically polished plane, and the light emitting surface 284 is disposed to make an angle α with respect to the reflecting surface 282. Furthermore, as shown in FIGS. 8C and 8D, the guard guide 260' can be attached on the light emitting surface 284 side of the light guide 232. Alternatively, the guard guide 260 may be attached on the light emitting surface 284 side of the light guide 232. The reflecting surface and the light emitting surface of the fourth embodiment can be replaced with the reflecting surface and the light emitting surface of the second or the third embodiment.

Fifth Embodiment

An infrared denaturing device according to a fifth embodiment of the present invention will be described. The infrared denaturing device according to the fifth embodiment is provided with a light guide and a light projecting body that are integrated like the fourth embodiment instead of the light guide and the light projecting body of the first embodiment, where the tip of said integrated light guide is further bent. In FIG. 9A is a side view of a light guide 280B integrated with a light projecting body, and 9B is a front view of the light guide 280B seen from its tip in the axial direction L'.

The light guide 280B shown in FIG. 9 is formed of a colorless transparent material which can transmit infrared light, for example, $SiO_2$ or $Al_2O_3$. The dimensions of the light guide 280 are, for example, a diameter of about 3.0-15 mm and a length of about 100-330 mm with a columnar shape. As shown in FIG. 9A, the light guide 280 has a bent part 281B that is bent with respect to the light guide 280 in the vicinity of the end that emits infrared light. The axial line L' of the bent part 281B makes a bending angle θ1 with respect to the axial line L of the light guide 280.

Both side surfaces of the bent part 281B are cut off on the tip side to form a pair of reflecting surfaces 282B. The outer periphery of each of the reflecting surfaces 242B on the side surface forms a parabola as shown in FIG. 9A. The tip surface of the bent part 281B is formed to have a narrow substantially rectangular light emitting surface 284B. As shown in FIG. 9B, the light emitting surface 284B is sandwiched between the pair of reflecting surfaces 282B. The light emitting surface 284B has an angle θ2 with respect to a plane vertical to the axial line L'. The light emitting surface 284B is generally rectangular in plan view. This angle θ may be set, for example, in a range of about 0°-45°. The angle θ2 can be made larger to make the area of the light emitting surface larger.

Sixth Embodiment

Figure 10:
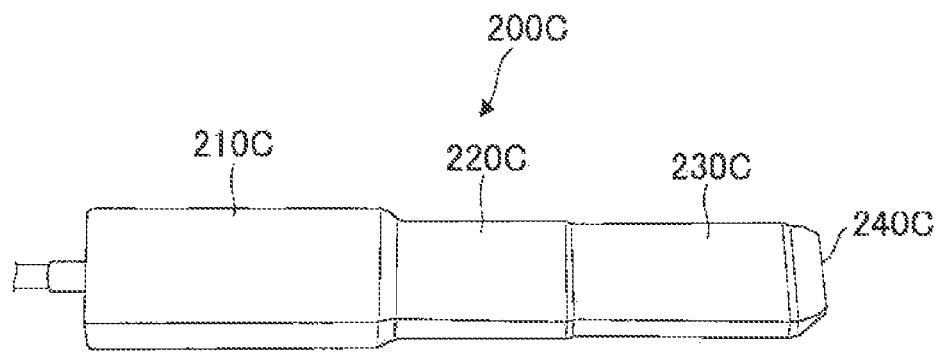
FIG. 10 A perspective view showing a handheld equipment according to a sixth embodiment.

An infrared denaturing device according to a sixth embodiment of the present invention will be described. The infrared denaturing device according to the sixth embodiment employs a handheld equipment 200C having a rectangular cross section instead of the handheld equipment 200 of the first embodiment. FIG. 10 is a perspective view of the handheld equipment 200C.

The handheld equipment 200C shown in FIG. 10 is provided with a hollow body part (lamp house) 210C for accommodating an infrared lamp, a grip member 220C connected to the right end (infrared outputting end) of the body part 210, a light guide accommodating member 230C connected to the right end (infrared outputting end) of the grip member 220C, and a light projecting body 240C disposed at the right end (infrared outputting end) of the light guide accommodating member 230C. The light emitting surface of the light projecting body 240C is substantially rectangular. The light projecting body 240C except the light emitting surface at its tip is preferably covered with a black resin cover. The light projecting body of the sixth embodiment may be configured like the light projecting body of any of the first to fourth embodiments, which is specifically as follows.

Similar to the light projecting body 240 of the first embodiment, a reflecting surface may be formed on the tip surface of the light projecting body 240C of the sixth embodiment while a light emitting surface is formed on the side surface of the light projecting body. Similar to the light projecting body 240A of the second embodiment, the tip of the light projecting body 240C of the fifth embodiment may be rounded with a plurality of conical recesses formed on the tip surface so as to form reflecting surfaces within the recesses and form a light emitting surface on the rounded tip around the recesses of the light projecting body. Similar to the light projecting body 240B of the third embodiment, a reflecting surface may be formed on the tip surface of the light projecting body 240C of the fifth embodiment and a pair of light emitting surfaces may be formed by cutting off both side surfaces of the light projecting body.

Seventh Embodiment

Figure 12:
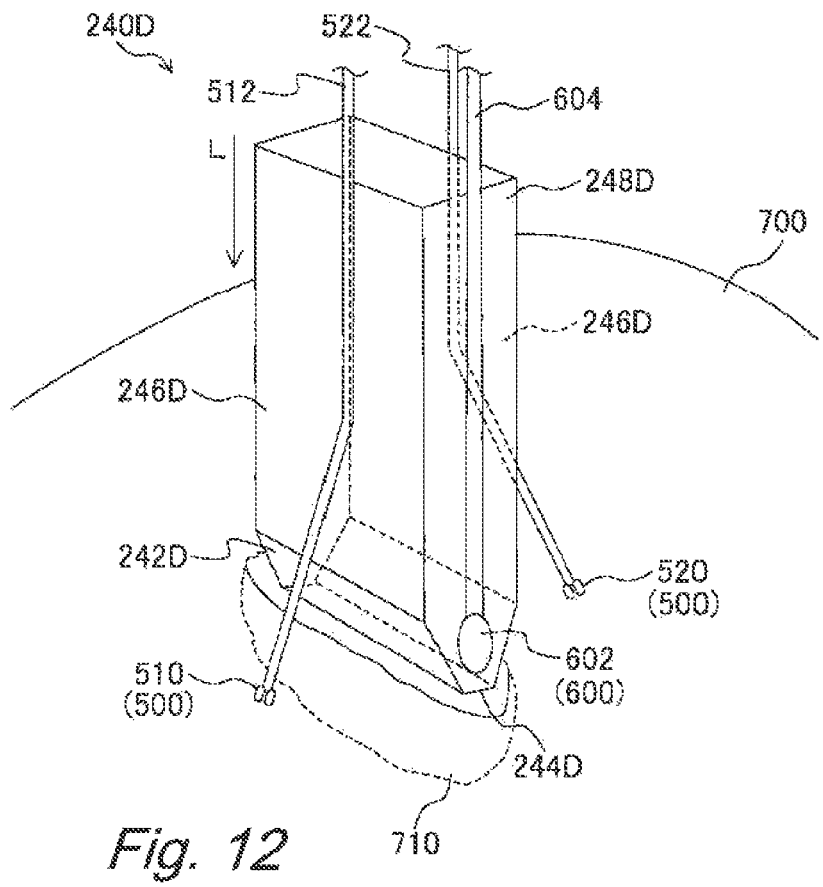
FIG. 12 A perspective view showing a light projecting body part of an infrared denaturing device according to a seventh embodiment.

An infrared denaturing device according to a seventh embodiment of the present invention will be described. The infrared denaturing device according to the seventh embodiment measures the coagulation degree of the tissue (transmurality of tissue) resulting from infrared irradiation and/or measures the temperature of the tissue to be coagulated so as to use either one or both of them to control the infrared irradiation. FIG. 12 shows only a light projecting body 240D and its surroundings of the infrared denaturing device according to the seventh embodiment, and a handheld equipment 200 (grip member 220), a device body 100 and else are not shown. The parts not shown may have a similar structure as the first embodiment. The light projecting body 240D is provided with a pair of reflecting surfaces 242D inclined to a longitudinal direction (incident direction of infrared light) L, and a light emitting surface 244D sandwiched between the pair of reflecting surfaces 242D. The reflecting surfaces 242D and/or the light emitting surface 244D have a rectangular or elongated shape. The light emitting surface 244D may be, for example, a rectangular having short sides of about 10 mm and long sides of about 30 mm.

Figure 13:
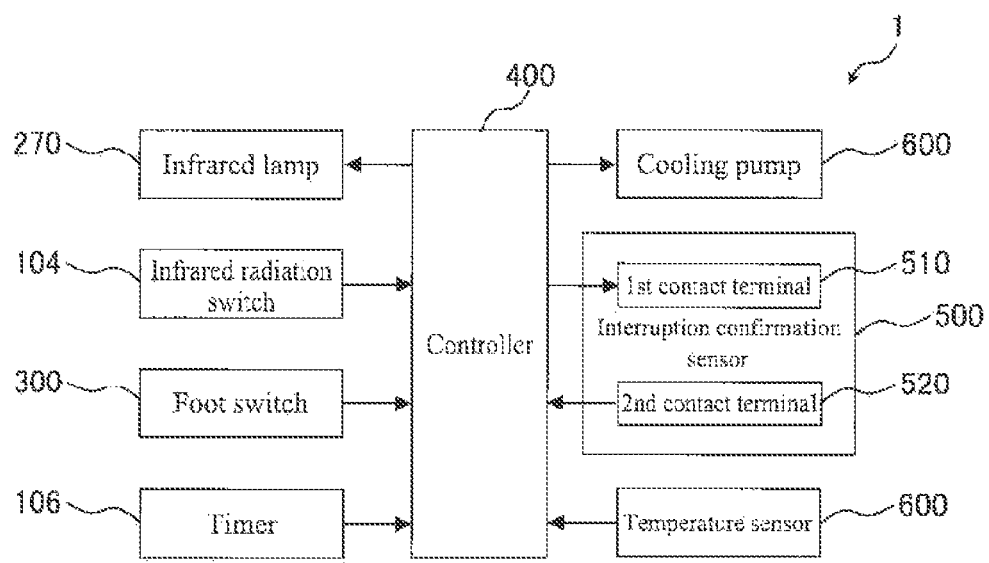
FIG. 13 A block diagram of the infrared denaturing device according to the seventh embodiment.

The light projecting body 240D is provided with an abnormal conductive pathway interruption confirming sensor (denaturation detecting sensor) 500 and a temperature sensor 600, which are connected to a controller 400 shown in FIG. 13. The interruption confirming sensor 500 detects whether an abnormal conductive pathway interruptive block is sufficiently formed by infrared irradiation upon interruption of the abnormal conductive pathway of the myocardium with the infrared denaturing device of a seventh embodiment. The interruption confirming sensor 500 determines the mutual arrival time between tissues 700 such as a myocardium sandwiching a region to be coagulated (region being denatured) 710 using weak electrical stimulation. The interruption confirming sensor 500 is configured with a first contact terminal (pacing electrode) 510 for sending electrical stimulation to a tissue, and a second contact terminal (sensing electrode) 520 for receiving the electrical stimulation generated by the first contact terminal 510 by making contact with the tissue. The distance to the first contact terminal 510 or the second contact terminal 520 from the outer edge of the light emitting surface 244D may preferably be about 5-20 mm, and more preferably about 10 mm. Accordingly, the first contact terminal 510 or the second contact terminal 520 can be disposed at positions less susceptible to heat of the light emitting surface 244D.

The first contact terminal 510 and the second contact terminal 520 are disposed to sandwich the generally center of the light emitting surface 244D at the long sides of the light emitting surface 244D. A straight line connecting the first contact terminal 510 and the second contact terminal 520 is positioned generally vertical to or crosses the long sides of the light emitting surface 244D. The first contact terminal 510 is held at the tip of a first conductor 512 while the second contact terminal 520 is held at the tip of a second conductor 522. The first conductor 512 and the second conductor 522 are disposed to reach near or in front of the reflecting surface 242D along the wide side surfaces 246D of the light projecting body 240D. The first conductor 512 and the second conductor 522 is bent near or in front of the reflecting surface 242D to be positioned away from the wide side surfaces 246D of the light projecting body 240D.

The first contact terminal 510 and the second contact terminal 520 can make contact with the surface of the tissue 700 such as an epicardium at positions away from the outer edge of the light emitting surface 244D. The first contact terminal 510 and the second contact terminal 520 need to make contact with the surface of the tissue 700 outside the region to be coagulated 710. The first contact terminal 510 and/or the second contact terminal can preferably employ a bipolar conductive element. In order to determine the progress of tissue coagulation by infrared irradiation, the interruption confirming sensor 500 determines the change in the electrical conduction time between the tissues 700 sandwiching the region to be coagulated 710 and apply this change in the delay time to the confirmation of the interruptive blocking of an abnormal conductive pathway caused by arrhythmia, thereby confirming the outcome.

The temperature sensor 600 is configured with a temperature detection terminal 602 such as a thermocouple and a pair of temperature detection conductors 604 connected to the temperature detection terminal 602. The temperature detection terminal 602 is disposed in the vicinity of the light emitting surface 244D at the narrow side surface 248D of the light projecting body 246D while the temperature detection conductor 604 extends along the narrow side surface 248D and is connected to the controller 400.

A block diagram of the infrared denaturing device 1 according to the seventh embodiment of the present invention will be described with reference to FIG. 13. The controller 400 of the infrared denaturing device 1 is connected to an infrared lamp 270, an infrared radiation switch 104 for turning the infrared lamp 270 on and off, a foot switch 300 for turning the infrared lamp 270 on and off, a timer 106 for defining the radiation time of the infrared lamp 270, a cooling pump or a vacuum cooler (cooling mechanism) 600 for cooling the infrared lamp 270, the first contact terminal 510, the second contact terminal 520, and the temperature sensor 600. The controller 400 controls the operation of the infrared lamp 270 based on signals from the infrared radiation switch 104, the foot switch 300 and the timer 106. The controller 400 also controls the operation of the infrared lamp 270 and/or the cooling pump 600 based on the temperature of the light emitting surface 244D detected with the temperature sensor 600. Furthermore, the controller 400 sends a signal from the first contact terminal 510 to the tissue 700 and at the same time receives a signal conducted from the tissue 700 via the second contact terminal 520 to determine the conduction time so as to control the operation of the infrared lamp 270 according to the flowchart shown in FIG. 14 or 15. Additionally, the controller 400 comprises a stimulation conduction time measuring section (stimulation conduction time calculation program) which sends an electrical stimulation signal from outside the region being denatured via one (first) contact terminal 510 of the interruption confirming sensor 500 and calculates based on the conduction time of the electrical stimulation signal received by the other (second) contact terminal 520, and a radiation controller (radiation control program) which performs infrared radiation onto the light projecting body 240D at predetermined intervals or duty cycle.

According to the seventh embodiment, since the interruption confirming sensor 500 is used to individually determine interruption of the abnormal conductive pathway of the myocardium in the region to be coagulated 710, whether infrared irradiation should be prolonged can be notified using a display device or the like regardless of the difference in the myocardium thickness among the individuals. Here, once interruption of the abnormal conductive pathway is confirmed and the infrared irradiation should not be prolonged, it can be notified with an alarm or the like and the operation of the infrared lamp can be stopped. In addition, the temperature sensor 600 can be used to determine the temperature of the region to be coagulated 710 so that overheating (carbonization denaturation) can be notified with an alarm of the like, thereby stopping the operation of the infrared lamp. Accordingly, in the seventh embodiment, the interruption confirming sensor 500 and the temperature sensor 600 are used to confirm the influence and the effect of coagulation with the infrared denaturing device, thereby performing safety measures upon the operation.

In the seventh embodiment, the light emitting surface 244D, the first contact terminal 510 and the second contact terminal 520 are brought into contact with a tissue 700 such as a heart upon infrared irradiation. During coagulation with the infrared denaturing device, conduction time of several times of weak electrical stimulations between the first contact terminal 510 and the second contact terminal 520 is measured to detect the conduction time to stable at a predetermined value. Upon this detection, transmural interruptive coagulation targeted by MAZE surgery is judged to be completed and thus this treatment is ended. This signal is managed by the controller 400 of the device body 100 to prevent malfunctions upon use.

Figure 14:
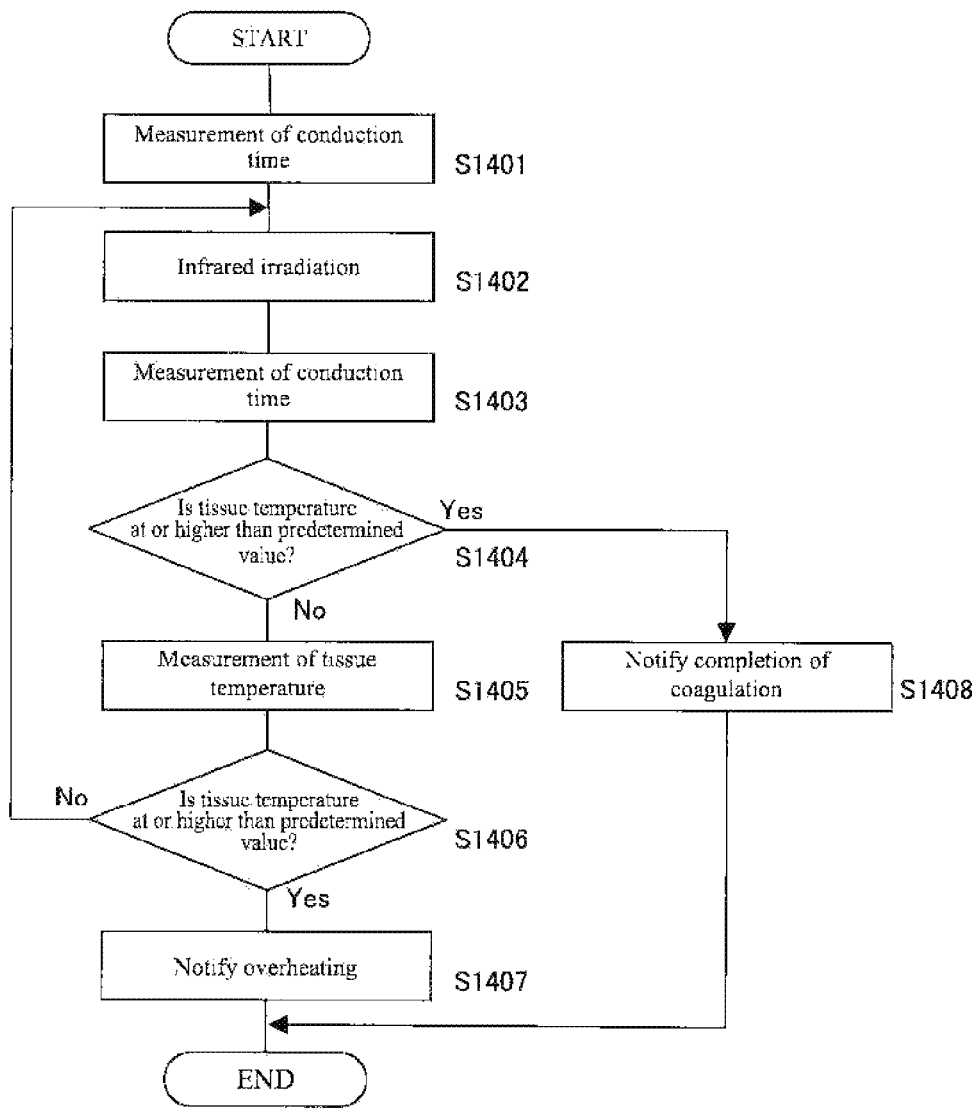
FIG. 14 A first flowchart of the infrared denaturing device according to the seventh embodiment.

A specific operation with the infrared device of the seventh embodiment will be described with reference to the first flowchart shown in FIG. 14. In Step S1401, the interruption confirming sensor 500 is used to measure the conduction time while the light emitting surface 244D, the first contact terminal 510 and the second contact terminal 520 are making contact with a region to be coagulated 710 of a tissue 700. Subsequently, in Step S1402, infrared light is emitted from the light emitting surface 244D onto the region to be coagulated 710 for a predetermined time. Following the infrared irradiation, the interruption confirming sensor 500 is used to measure the conduction time in Step 1403. Once the controller 400 judges that the conduction time is at or higher than a predetermined value for a predetermined period in Step 1404, proceed to Step 1408 to notify completion of coagulation and end coagulation of the region to be coagulated 710. Here, in the seventh embodiment, the phrase "conduction time is at or higher than a predetermined value for a predetermined period" means that the measured conduction time (delay value) is stable as represented by the post-radiation state C3 in FIG. 16.

If the controller 400 judges that the conduction time is less than the predetermined value for a predetermined period in Step 1404, then proceed to Step S1405. In Step S1405, the temperature sensor 600 measures the temperature at or near the region to be coagulated 710 and proceed to Step S1406. If the controller 400 judges that the temperature at or near the region to be coagulated 710 is at or higher than a predetermined value in Step S1406, then proceed to Step S1407 to notify overheating and end coagulation of the region to be coagulated 710. If the controller 400 judges that the tissue temperature is less than the predetermined value in Step S1406, meaning that the temperature is low and coagulation is insufficient, proceed to Step S1402 to repeat the coagulation operation for the same region to be coagulated 710. The predetermined value of the tissue temperature defined in Step S1406 refers to a temperature that allows progress of stable coagulation while preventing carbonization denaturation of the region to be coagulated, which can variably be adjusted preferably in a range of 50° C.-120° C. Thus, using the temperature sensor 600, the controller 400 can automatically control the temperature rise on the light emitting surface at the device body. The infrared irradiation (Step S1402) in the flowchart shown in FIG. 14 is carried out at predetermined intervals or duty cycle.

Figure 15:
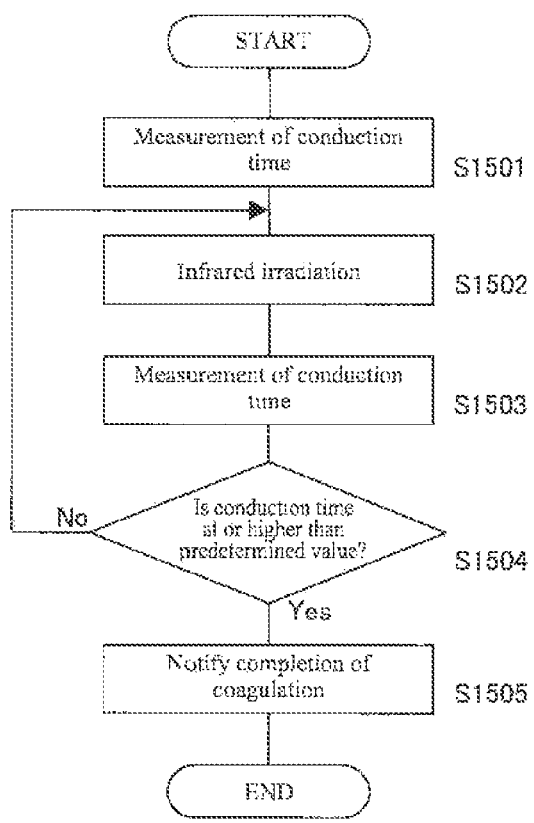
FIG. 15 A second flowchart of the infrared denaturing device according to the seventh embodiment.

A specific operation of the infrared device of the seventh embodiment without the temperature sensor 600 will be described with reference to the second flowchart shown in FIG. 15. In Step S1501, the interruption confirming sensor 500 is used to measure the conduction time while the light emitting surface 244D, the first contact terminal 510 and the second contact terminal 520 are making contact with a region to be coagulated 710 of a tissue 700. Subsequently, in Step S1502, infrared light is emitted from the light emitting surface 244D onto the region to be coagulated 710 for a predetermined period of time. Following the infrared pulse radiation, the interruption confirming sensor 500 is used to measure the conduction time in Step 1503. Once the controller 400 judges that the conduction time is at or higher than a predetermined value for a predetermined period in Step S1504, proceed to Step S1505 to notify completion of coagulation and end coagulation of the region to be coagulated 710. If the controller 400 judges that the conduction time is less than the predetermined value for a predetermined period in Step 1504, meaning that the temperature is low and coagulation is insufficient, proceed to Step S1502 to repeat the coagulation operation for the same region to be coagulated 710. The infrared irradiation (Step S1502) in the flowchart shown in FIG. 15 is carried out at predetermined intervals or duty cycle.

The technical feature as a premise of the seventh embodiment of the present invention is to efficiently generate tissue coagulation to the deep layer part of the living body. Therefore, an energy source and a transmission mechanism thereof for providing deep coagulation to the deep layer part are the primarily selected conditions. The next requirement is the operation method of them, that is, how to provide its energy to a target. A perennial problem upon this execution is carbonization denaturation (blackening) in a part of the region irradiated with the energy source. This carbonization denaturation is a tissue denaturation caused by heat that inevitably occurs during the course of excessive coagulation. Once this phenomenon occurs, locally extreme energy absorption is caused in most of the energy sources typified by electric energy and laser, making it difficult to obtain a stable coagulation depth. Since energy sources with higher directivity such as laser have higher energy density at the center, they are associated with the problem of carbonization denaturation. In particular, it is a major issue in operating an infrared denaturing device that this problem is likely to occur with relatively wide coagulation that exceeds about 10 millimeters on the surface layer. Therefore, for a therapeutic purpose that requires management of deep coagulation that exceeds about 10 millimeters on the surface layer, the present invention intentionally employs an infrared lamp light that has high diffusion effect so that distribution of the output density on the light emitting surface is averaged to be generally low, and infrared irradiation is controlled based on the temperature detected with the temperature sensor 600 so as to control the radiation environment of the light emitting surface making contact to be, for example, about 120-100° C. or less.

As shown in FIG. 12, the pair of temperature detection conductors 604 of the temperature sensor 600 extend from the device body 100 through the handheld equipment 200 and connected to the temperature detection terminal 602 disposed near the light emitting end surface 244D at the side surface of the light projecting body. Upon operating the infrared denaturing device, the controller 400 performs output management according to the predetermined conditions based on the temperature information measured by the temperature sensor 600 in real time so as to manage approximate coagulation depth on the contact surface for several tens of seconds while preventing carbonization denaturation (Steps S1405-S1407 in FIG. 14). The conditions for realizing such stable depth management are firstly that the output density distribution on the light emitting surface 244D is generally averaged, secondly that the control is easy under an environment at a temperature that does not cause carbonization denaturation of the tissue (for example, a temperature of about 120-100° C. or lower), and thirdly that the operation time per shot (1 site) is in a several tens second level. If the operation time takes a minute to several minutes, convenience is lowered. In the controller 400, correction calculation of the base value of the output density is performed in advance for each infrared denaturing device 1 (handheld equipment 200) used to store the value acquired by correction calculation. The approximate coagulation depth can be estimated by adding a supply output and radiation time to this correction calculation value.

In the seventh embodiment, the controller 400 can also notify the approximate progress of the coagulation depth to the operator in real time with a display device such as a display or a notify device such as a speaker. Here, the progress is calculated by the controller 400 based on the output density, output conditions, radiation time and the like of each handheld equipment 200.

Figure 18:
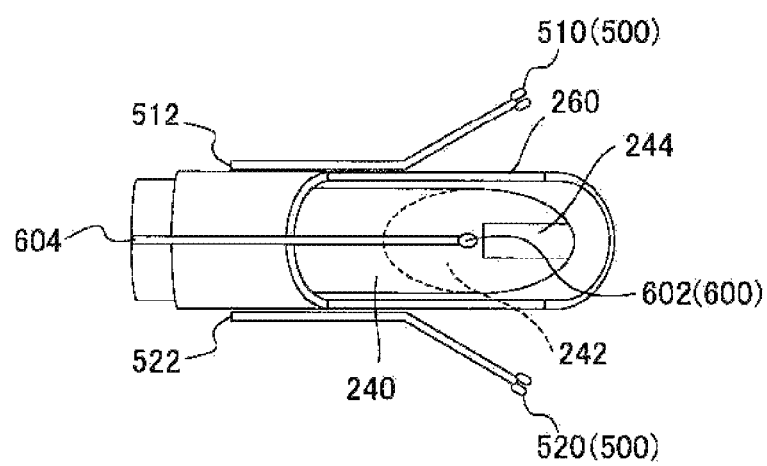
FIG. 18 A front view showing a light projecting body part of an infrared denaturing device according to an eighth embodiment.

Although the interruption confirming sensor 500 and/or the temperature sensor 600 are provided in the light projecting body 240D of the seventh embodiment, it is not limited thereto and any of the light projecting bodies of the first to sixth embodiments can be provided with the interruption confirming sensor 500 and/or the temperature sensor 600. For example, a light projecting body of an eighth embodiment shown in FIG. 18 is a light projecting body 240 of the first embodiment provided with an interruption confirming sensor 500 (first contact terminal 510, first conductor 512, second contact terminal 520 and second conductor 522) and/or a temperature sensor 600 (temperature detection terminal 602 and temperature detection conductor 604). The interruption confirming sensor 500 and/or the temperature sensor 600 may be disposed on the surface of the guard guide 260, or on the surface of the light projecting body 240.

Although the infrared lamp 270 was used as the infrared light source in the infrared coagulators of the first to eighth embodiments, it is not limited thereto, and an infrared LED may also be used as the infrared light source. An infrared lamp generates visible light as well as infrared light, which is dazzling to the operator and makes it difficult to see the region to be coagulated. Accordingly, in the infrared coagulators of the first to eighth embodiments, an optical filter for partially removing the visible light can be provided between the infrared lamp and the light projecting body or on the light emitting surface.

[Summary]

The infrared denaturing device of the present invention can be used so that number of treatments that have been impossible until now become newly available. The following four points become available: (1) irradiation with the infrared denaturing device on a beating heart (thoracoscopically) from the epicardium side along the cutting and suturing line for a conventional atrial fibrillation surgery without stopping or opening the heart, or without extracorporeally circulating blood; (2) irradiation for ventricular arrhythmia via an epicardial approach; (3) cautery of infective wound for infectious endocarditis; and (4) irradiation of cardiac tumor.

In addition, the followings become available as newly possible treatments: (1) realizing thoracoscopic electrical isolation from the atrial free wall that has been impossible; (2) ensuring success of substrate ablation for ventricular fatal arrhythmia in a short time that has conventionally been performed with a catheter; and (3) realizing coagulation treatment or thermotherapy for seeking local necrosis of multiple tumors without the need of excision. Accordingly, new treatment methods can be expected to result further shortening of the treatment time and enhancement of therapeutic quality.

The infrared denaturing device of the present invention is capable of generating deep transmural coagulation in a relatively long linear region that extends for more than 10 millimeters without the concern of carbonization denaturation. Therefore, a clinician of cardiovascular surgery can generate transmural coagulation in the atrium (ventricle) of a normothermic beating heart for an abdominal and thoracoscopic cardiac surgery. More specifically, the present invention (1) can be employed for a coagulation treatment intended for interrupting an abnormal conductive pathway of arrhythmia such as atrial fibrillation and atrial flutter, and (2) can perform accurately managed continuous coagulation onto a targeted site weakened due to a tumor and having unclear contamination environment, for example, infectious endocarditis or excised face of a cardiac tumor.

The infrared denaturing device of the present invention utilizes near infrared light to realize an abdominal or thoracoscopic coagulation treatment of a myocardium in a cardiac surgery. The coagulation treatment of the myocardium can be achieved by cytologically necrosing a part of the myocardium without impairing the shape and the functions of the heart. Being capable of easily creating stable coagulation that can easily be managed in the depth direction of the coagulation using the device of the present invention is an important point during the surgery and also for prognosis in terms of metastasis. In particular, while many free ends would exist to allow the target to freely escape in a thoracoscopic approach from the epicardial side, the infrared denaturing device of the present invention is capable of instantaneously creating coagulation of interest through a terminal contact at only one side, and thus the use thereof expands widely. The infrared denaturing device of the present invention can perform continuous coagulation that is accurately managed for a wide range of target onto a tissue weakened due to a tumor and having unclear contamination boundary without spreading the contaminated area.

The infrared denaturing device of the present invention can perform light coagulation onto a tissue that makes contact with or that faces the light emitting surface in a frontal direction (e.g., the second, third and fifth embodiments) or a lateral direction (e.g., the first and fourth embodiments) with respect to the tip of the light guide having a diameter of about 10 mm. The shape of the coagulation is defined by the shape of the light emitting surface, and the coagulation depth can be controlled with the timer 106 for a unit of several seconds or between about 1-30 seconds. Deep, generally hemispherical coagulation having a cross section with a clear boundary can continuously be created in several seconds. Accordingly, the operator can easily predict the effect of the coagulation on the back layer, and thus the treatment in the deep layer part of the coagulation can be prevented from being missed.

In each embodiment of the present invention, the light projecting body preferably has an elongated light emitting surface with a size of about 5.0 mm×about 40 mm (or a substantially identical area) and performs continuous irradiation by moving the light emitting surface such that the tissue can be cauterized in a linear or belt-like manner.

In the embodiments of the present invention, a bipolar conductive element is installed at the height of the light emitting surface of the handheld equipment so as to sandwich the coagulated region where it is less susceptible to a thermal effect so that it can be utilized to measure the change in the delay of the conduction time. Thus, MAZE surgery can safely be conducted by mechanically confirming the outcome of the interruption of abnormal conductive pathway of arrhythmia resulting from coagulation.

In the embodiments of the present invention, a temperature sensor may be installed near the light emitting surface of the handheld equipment to feedback this information to the device body in real time. In the device body, the output density distribution on the light emitting surface of each handheld equipment is corrected to the base value so as to adjust the output and the radiation time at a predetermined temperature under management. Thus, a safe operation can be carried out while mechanically notifying the change in the approximate coagulation depth to the operator.

EXAMPLE

An example using the infrared denaturing device of the seventh embodiment will be described. In this example, a case of a 64-year-old male with severe MR, TR and Paf received a MAZE surgery that combined mitral and tricuspid valvuloplasty and infrared coagulation.

Figure 17:
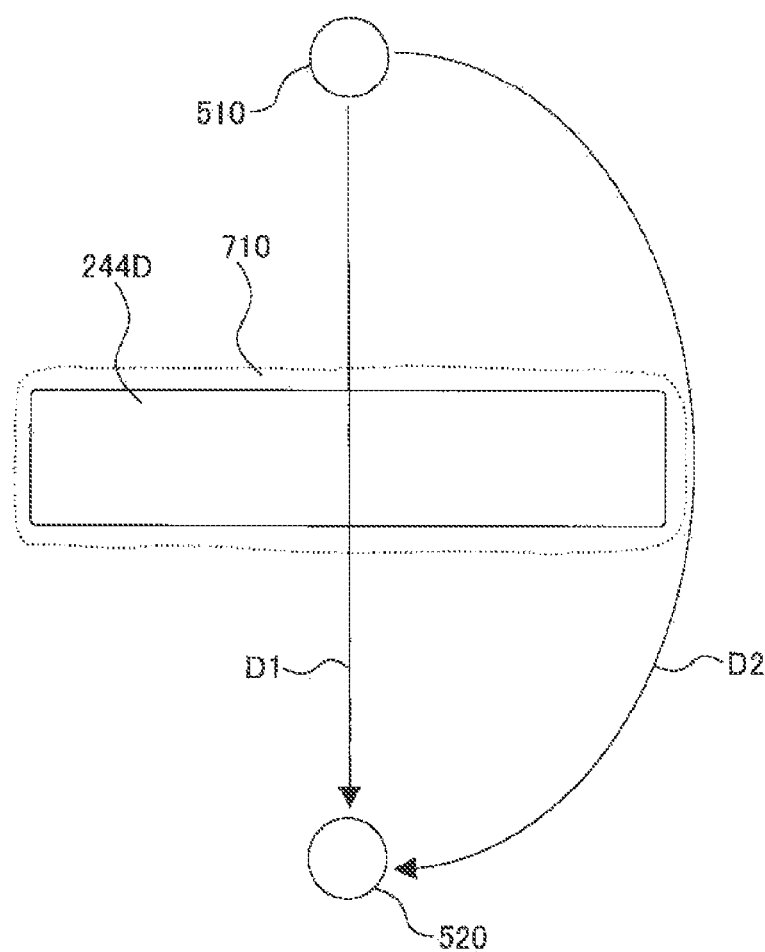
FIG. 17 A schematic view for determining a conductive delay rate according to the example shown in FIG. 16.

As shown in FIG. 17, the light emitting surface 244D of the infrared denaturing device of the seventh embodiment was pressed onto the surface of a region to be coagulated 710 for infrared radiation. Moreover, in order to measure the stimulation conduction time, a pacing electrode (first contact terminal 510) and a sensing electrode (second contact terminal 520) made contact at positions 10 mm apart from the coagulation line (outer edge) of the light emitting surface 244D. A coagulation process was performed by running 5 sets (30 seconds) of about 4 seconds of infrared irradiation and about 2 seconds of interval. An electrophysiology study (EPS) was conducted for evaluation. The conduction time in the atrium was successively measured before, during and after the irradiation under overdrive pacing (FIG. 15). Next, the predicted post-radiation conductive delay rate calculated from the conductive distance was compared to the actually measured conductive delay rate. In addition, the pacing electrode was attached to the end of the right auricle while the sensing electrode was attached to the right ventricular free wall to irradiate the root of the right auricle under overdrive pacing. Pathological findings of the coagulated free wall were observed.

Figure 16:
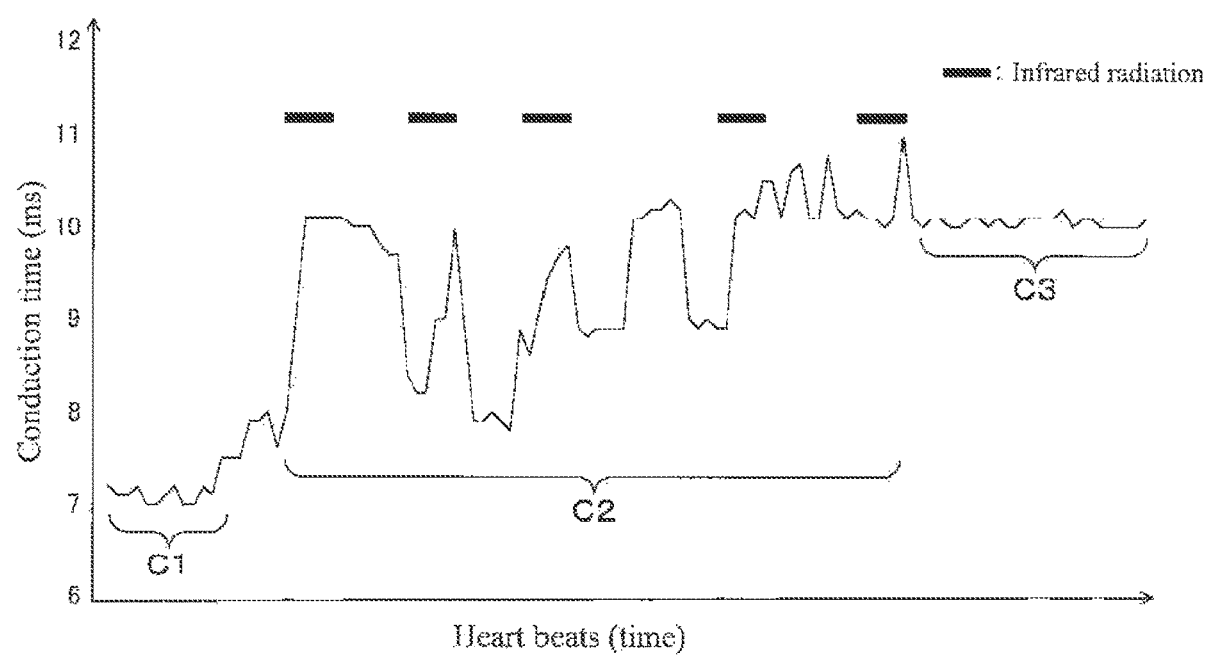
FIG. 16 A graph showing changes in the conduction time with infrared irradiation according to an example of the present invention.

As shown in FIG. 16, the stimulation conduction time was about 7.0 ms in the pre-radiation state C1, 8-10 ms in the radiation state C2, and about 10.0 ms in the post-radiation state C3. The conductive delay rates were such that prediction:actual measurement during radiation:actual measurement after radiation=1.55:1.57:1.43. If was confirmed from the conduction time that the region to be coagulated 710 changed from a reversible block to an irreversible block during the irradiation.

In FIG. 17, the pre-radiation stimulation conductive distance D1 was 30 mm while the post-radiation stimulation conductive distance D2 was 46 mm. The predicted conductive distance delay rate was calculated to be 46 mm/30 mm=about 1.55. In the meantime, an actually measured conductive distance delay rate after the irradiation was determined to be 10 ms/7 ms=about 1.43. Parts observed with transmural coagulation and parts not observed with transmural coagulation coexisted. Creation of an electrical block of the atrial free wall by infrared irradiation on the beating heart was clinically confirmed.

As can be appreciated from FIG. 16, the conduction time that was 7.0 milliseconds before the surgery was stabilized at about 10.0 ms after the treatment. From this, a local transmural coagulation block was assumed to be completed via an approach from the outer layer of the myocardium, from anatomical and electrophysiological judgements.

The invention claimed is:

1. An infrared denaturing device for denaturing an object to be denatured with infrared light, the infrared denaturing device comprising an infrared light source for emitting non-directional infrared light, a light projecting body for irradiating a region being denatured of the object to be denatured with infrared light, and a controller for controlling operation of the infrared light source,
    wherein the light projecting body is provided, at its tip on a light emitting side, with at least one pair of a reflecting surface for reflecting and guiding infrared light from the infrared light source to the region being denatured and a light emitting surface for emitting the infrared light reflected by the reflecting surface onto the region being denatured,
    wherein the infrared denaturing device is provided with a denaturation detecting sensor for detecting infrared denaturation of the region being denatured,
    wherein the pair of the reflecting surface and the light emitting surface comprises a pair of a first reflecting surface and a first light emitting surface, or a pair of a second reflecting surface and a second light emitting surface; and
    wherein the first reflecting surface is inclined to a light guide axis of the infrared light from the infrared light source to the light projecting body, and the first light emitting surface is disposed in parallel to the light guide axis, and the second reflecting surface is a pair of second reflecting surfaces formed at a tip of the light projecting body, and the second light emitting surface is disposed between the pair of the second reflecting surfaces and formed at a right angle or inclined to a light guide axis.

2. The infrared denaturing device according to claim 1, wherein the denaturation detecting sensor is an electrical stimulation interruption confirming sensor for confirming interruption of electrical stimulation in the region being denatured.

3. The infrared denaturing device according to claim 2, wherein the interruption confirming sensor comprises, in a vicinity of the region being denatured, a pair of contact terminals that are adapted to make contact with the object to be denatured.

4. The infrared denaturing device according to claim 3, wherein the pair of contact terminals are disposed to sandwich the light emitting surface at long sides of the light emitting surface.

5. The infrared denaturing device according to claim 3, wherein the interruption confirming sensor measures conduction time of electrical stimulation between the pair of contact terminals.

6. The infrared denaturing device according to claim 5, wherein the controller judges completion of denaturation of the region being denatured based on the conduction time.

7. The infrared denaturing device according to claim 3, wherein the pair of contact terminals are disposed distant from the light emitting surface so as to avoid influence of the infrared light from the light emitting surface.

8. The infrared denaturing device according to claim 1, further comprising a temperature sensor for measuring a temperature of the region being denatured or the light emitting surface.

9. The infrared denaturing device according to claim 8, further comprising a timer for defining a radiation time of the infrared light, wherein the controller stores an output density of the infrared light and calculates a coagulation depth of the region being denatured by using temperature information acquired with the temperature sensor and the output density and the radiation time.

10. The infrared denaturing device according to claim 9, comprising a display device for displaying the calculated coagulation depth.

11. The infrared denaturing device according to claim 1, wherein at least one of the first light emitting surface and the second light emitting surface has long sides of 8-40 mm.

12. The infrared denaturing device according to claim 1, wherein at least one of the first reflecting surface and the second reflecting surface diffuses, disperses or totally reflects the infrared light from the infrared light source.

13. The infrared denaturing device according to claim 1, wherein a light guide for guiding infrared light emitted from the infrared light source to the light projecting body is integrally formed with the light projecting body.

14. The infrared denaturing device according to claim 13, wherein the light guide is a rectangular prism with a rectangular cross section, the reflecting surface is a pair of reflecting surfaces provided at long sides of a tip on the light emitting side, and the light emitting surface is a rectangular light emitting surface formed between the pair of reflecting surfaces.

15. The infrared denaturing device according to claim 1, comprising a heat-proof guard guide provided at a tip of the light projecting body on the light emitting side in order to prevent infrared irradiation of the region not being denatured of the object to be denatured.

16. The infrared denaturing device according to claim 15, wherein the guard guide is provided with a notch for irradiating the region being denatured with infrared light.

17. An infrared denaturing method for denaturing an object to be denatured with infrared light by using the infrared denaturing device according to claim 1, the method comprising an irradiation step of irradiating the region being denatured with infrared light while pressing the light emitting surface onto the surface of the region being denatured of the object to be denatured.

18. The infrared denaturing method according to claim 17, wherein the irradiation step is repeated for multiple times to form an elongated denatured region.

19. The infrared denaturing method according to claim 1, wherein the object to be denatured is a heart, and the irradiation step comprises irradiating the region being denatured of the object to be denatured with infrared light while pressing the light emitting surface onto the heart from an epicardium side.

20. The infrared denaturing method according to claim 19, wherein the irradiation step is carried out under a beating heart condition.

21. An infrared denaturing device for denaturing an object to be denatured with infrared light, the infrared denaturing device comprising an infrared light source for generating non-directional infrared light, a light projecting body for irradiating a region being denatured of the object to be denatured with infrared light, and a controller for controlling operation of the infrared light source,
    wherein the light projecting body is provided, at its tip on the light emitting side, with at least one pair of a reflecting and guiding surface for reflecting infrared light from the infrared light source to the region being denatured and an elongated light emitting surface for emitting the infrared light reflected by the reflecting surface onto the region being denatured,
    wherein the pair of the reflecting surface and the light emitting surface comprises a pair of a first reflecting surface and a first light emitting surface, or a pair of a second reflecting surface and a second light emitting surface; and
    wherein the first reflecting surface is inclined to a light guide axis of the infrared light from the infrared light source to the light projecting body, and the first light emitting surface is disposed in parallel to the light guide axis, and the second reflecting surface is a pair of second reflecting surfaces formed at a tip of the light projecting body, and the second light emitting surface is disposed between the pair of the second reflecting surfaces and formed at a right angle or inclined to a light guide axis.

22. An infrared denaturing device for denaturing an object to be denatured with infrared light, the device comprising:
    a light projecting body for emitting the infrared light while making contact, in a rectangular shape, with a region being denatured of the object to be denatured;
    an interruption confirming sensor having a pair of contact terminals that are distantly disposed outside the region being denatured along a line crossing a longitudinal direction of a contact part of the light projecting body; and
    a controller provided with a stimulation conduction time measuring section for carrying out measurement based on conduction time of an electrical stimulation signal that is sent from outside the region being denatured via the first contact terminal of the interruption confirming sensor and that is received with the second contact terminal, and a radiation controller for emitting infrared light to the light projecting body at predetermined intervals or duty cycle,
    wherein the light projecting body is provided, at its tip on a light emitting side, with at least one pair of a reflecting surface for reflecting and guiding infrared light from an infrared light source to the region being denatured and a light emitting surface for emitting the infrared light reflected by the reflecting surface onto the region being denatured; and
    wherein the reflecting surface is a pair of reflecting surfaces formed at a tip of the light projecting body, and the light emitting surface is disposed between the pair of the reflecting surfaces and formed at a right angle or inclined to a light guide axis.

23. A method for controlling irradiation by an infrared denaturing device for denaturing an object to be denatured with infrared light, the method comprising the steps of:
    irradiating a region being denatured of the object to be denatured with infrared light at predetermined intervals or duty cycle while allowing a light projecting body to make contact therewith in a rectangular shape; sending an electrical stimulation signal to a first contact terminal of a pair of contact terminals that are distantly disposed outside the region being denatured along a line crossing a longitudinal direction of a contact part of the light projecting body;
    receiving a conduction signal of the electrical stimulation signal sent to the object to be denatured on an opposite side relative to a longitudinal direction of the rectangular light projecting body; and
    judging completion of coagulation by infrared denaturation after detecting stability of conduction time during and after an operation with respect to the conduction time of the electrical stimulation signal before the operation, wherein the light projecting body is provided, at its tip on a light emitting side, with at least one pair of a reflecting surface for reflecting and guiding infrared light from an infrared light source to the region being denatured and a light emitting surface for emitting the infrared light reflected by the reflecting surface onto the region being denatured; and wherein the reflecting surface is a pair of reflecting surfaces formed at a tip of the light projecting body, and the light emitting surface is disposed between the pair of the reflecting surfaces and formed at a right angle or inclined to a light guide axis.

\* \* \* \* \*